United States Patent [19]

Bequette et al.

[11] Patent Number: 5,372,823
[45] Date of Patent: Dec. 13, 1994

[54] DIRECT COMPRESSION CHOLESTYRAMINE TABLET AND SOLVENT-FREE COATING THEREOF

[75] Inventors: Robert J. Bequette; Bruce A. Bonenberger, both of Evansville; Claude E. Gallian, Newburgh; John R. Reckelhoff, Evansville, all of Ind.

[73] Assignee: Bristol-Myers Squibb Company, New York, N.Y.

[21] Appl. No.: 965,096

[22] Filed: Oct. 22, 1992

Related U.S. Application Data

[63] Continuation of Ser. No. 764,115, Sep. 23, 1991, abandoned, which is a continuation of Ser. No. 573,959, Aug. 27, 1990, abandoned, which is a continuation-in-part of Ser. No. 324,167, Mar. 16, 1989, Pat. No. 4,956,182.

[51] Int. Cl.$^5$ .......................... A61K 9/20; A61K 9/16
[52] U.S. Cl. .................................. 424/464; 424/78.1; 424/474; 424/476; 424/482; 424/489
[58] Field of Search ............... 424/464, 474, 476, 482, 424/489, 78.1

[56] References Cited

U.S. PATENT DOCUMENTS

| | | |
|---|---|---|
| 3,383,237 | 5/1968 | Tuerck et al. |
| 4,797,288 | 1/1989 | Sharma et al. |
| 4,814,354 | 3/1989 | Ghebre-Sellassie et al. |
| 4,843,098 | 6/1989 | Shaw et al. ..................... 424/476 |
| 4,882,160 | 11/1989 | Yang et al. ..................... 424/476 |
| 4,894,234 | 1/1990 | Sharma et al. ................. 424/476 |
| 4,895,723 | 1/1990 | Amer et al. |
| 4,956,182 | 9/1990 | Bequette et al. ............... 424/476 |

FOREIGN PATENT DOCUMENTS

| | | |
|---|---|---|
| 0037740 | 10/1981 | European Pat. Off. |
| 0040590 | 11/1981 | European Pat. Off. |
| 0261693 | 3/1988 | European Pat. Off. |
| 0595444 | 12/1947 | United Kingdom. |

OTHER PUBLICATIONS

Pharmaceutical Dosage Forms-Tablets, vol. 1, H. A. Lieberman and L. Lachman, Marcel Dekker, Inc., New York and Basel, pp. 112–173.

Pharmaceutical Technology/Fundamental Pharmaceutics, E. L. Parrott, Ph.D. Burgess Publishing Company, Minneapolis, Minn., pp. 74–79.

Remington's Pharmaceutical Sciences, Eighteenth Edition-1990, Philadelphia College of Pharmacy and Science, pp. 1641–1646.

Tuerck, et al., "Formula Modifications in a Solvent-Free Tablet Film Coat", J. Pharm. Sci. (1973) 62:1534–1537.

Jacobsen, et al., "Effect of enterocoated cholestyramine on bowel habit after ileal resection: a double blind crossover study" Britis Medical Journal (1985) 290:1315–1318.

Physician'Desk Reference (1967) 839–840.

Primary Examiner—Thurman K. Page
Assistant Examiner—Amy Hulina
Attorney, Agent, or Firm—Thomas R. Savitsky; Robert H. Uloth

[57] ABSTRACT

A directly compressed cholestyramine tablet with a solvent-free coating is disclosed. The inner core of the tablet is made up of cholestyramine agglomerates consisting of numerous small, irregularly-shaped, jagged-edged fragments having relatively few smooth or flat surfaces with a moisture content ranging from about 8 to 14 percent by weight. A process is also disclosed for preparing cholestyramine agglomerates of the invention. The solvent-free coating comprises from about 60 percent to about 95 percent by weight of stearic acid and from about 5 percent to about 40 percent of polyethylene glycol.

5 Claims, 6 Drawing Sheets

THE EFFECT OF MOISTURE AND COMPRESSION FORCE ON AVERAGE TABLET HARDNESS FOR 1.0 G CHOLESTYRAMINE TABLETS

THE EFFECT OF MOISTURE AND COMPRESSION FORCE ON AVERAGE TABLET HARDNESS FOR 1.0 G CHOLESTYRAMINE TABLETS

THE EFFECT OF INCREASING MOISTURE CONTENT ON OVERDRIED CHOLESTYRAMINE AGGLOMERATES FOR 1.0 G CHOLESTYRAMINE TABLETS

THE EFFECT OF MOISTURE AND COMPRESSION FORCE ON AVERAGE TABLET HARDNESS FOR 1.0 G CHOLESTYRAMINE TABLETS

THE EFFECT OF INCREASING MOISTURE CONTENT OF OVERDRIED CHOLESTYRAMINE AGGLOMERATES FOR 1.0 G CHOLESTYRAMINE TABLETS

THE RELATIONSHIP BETWEEN
COMPRESSION FORCE AND HARDNESS

KEY ■ Z0620 ◊ AMBERLITE AGGLOMERATES △ R1734

COMPRESSION PROFILES OF DIRECTLY COMPRESSED CHOLESTYRAMINE TABLETS MADE WITH CHOLESTYRAMINE AGGLOMERATES AND AMBERLITE POWDERED RESIN (R1734)

DOWEX 1-X2 CHOLESTYRAMINE RESIN BEADLETS

AMBERLITE XE-268P CHOLESTYRAMINE RESIN BEADLETS

CHOLESTYRAMINE AGGLOMERATES PREPARED FROM DOWEX 1-X2 RESIN BEADLETS

CHOLESTYRAMINE AGGLOMERATES PREPARED FROM AMBERLITE XE-268P RESIN BEADLETS

AMBERLITE XE-268P RESIN POWDER

DIRECT COMPRESSION CHOLESTYRAMINE TABLET AND SOLVENT-FREE COATING THEREOF

CROSS REFERENCE TO RELATED APPLICATIONS

This application is a continuation of application Ser. No. 07/764,115, filed Sep. 23, 1991, now abandoned, which is a continuation of application Ser. No. 07/573,959, filed Aug. 27, 1990, now abandoned, which is a continuation-in-part of application Ser. No. 07/324,167, filed Mar. 16, 1989, now U.S. Pat. No. 4,956,182.

BACKGROUND OF THE INVENTION

Cholestyramine resin powder, which is the chloride salt of a basic anion exchange resin, is a cholesterol lowering agent intended for oral administration. Although cholestyramine is quite hydrophilic, it is insoluble in water and is not absorbed from the digestive tract. Cholestyramine is marketed by the Bristol-Myers Company as a powder under the tradename QUESTRAN. The powder is not taken in its dry form, but is always mixed with water or other fluids before ingesting. The recommended adult dose is four grams of cholestyramine resin from one to six times daily. QUESTRAN is available as a powder in packets of nine grams, four of which are relatively anhydrous cholestyramine resin. The remaining five grams comprise other additives such as sucrose, flavoring and other ingredients to make the powder more palatable.

Obviously, it would be greatly desirable if cholestyramine resin could be put into tablet form, thereby eliminating the need for both mixing the powder in water before ingesting, and adding additional materials to render the product palatable. It would be even more desirable if the cholestyramine resin could be rendered directly compressible into a tablet, since direct compression is by far the desired tableting method, when compared to either wet or dry granulation methods. However, only a very limited number of pharmaceutical substances possess enough cohesive strength and flowability to allow direct compression without previous granulation. In fact, it is estimated that only about 20 percent of all materials used for tableting in the pharmaceutical field may be directly compressed. In order to use this method to a greater extent, many more materials are modified either by treating the material in some special way during early stages of preparation, or by adding a direct compression vehicle that mixes with the active ingredient and forms a flowable and easily compressible mixture. It is, of course, desirable to be able to directly compress a composition without addition of direct compression vehicles. Thus, it would be desirable to be able to directly compress cholestyramine resin into a tablet, preferably without the aid of direct compression vehicles.

Even if one were to successfully directly compress cholestyramine into a tablet, there is an additional problem that must still be overcome. Cholestyramine is extremely hygroscopic, which makes cholestyramine tablets very difficult to swallow. A cholestyramine tablet placed in the mouth swells rapidly by readily taking up the available moisture. A very dry mouth results and the tablet adheres to the tongue, and thus cannot be comfortably swallowed. Accordingly, it would be desirable to coat the tablet so as to render it easy to swallow.

Attempts to coat cholestyramine tablets, however, encounter difficulties because coatings normally comprise either water or an organic solvent. It is impossible to coat cholestyramine tablets with a water-based coating because the hygroscopic tablets would swell during the coating process. Although it is not difficult to coat cholestyramine with a solvent-based coating, cholestyramine has an affinity for the solvent which is retained even after the drying processes. That is, the cholestyramine resin retains the solvent in the tablet matrix itself at levels generally considered unacceptable. Such solvents often include an alcohol (e.g., ethanol) and methylene chloride. While retained alcohol might be acceptable, retained methylene chloride is not. Thus, there is a need for a coating which is neither water nor solvent based, and which imparts swallowability to cholestyramine or other pharmaceutical tablets.

U.S. Pat. No. 3,383,237 to Tuerck teaches a solvent-free coating applied in a molten state at temperatures of 60° C. to 130° C. Tuerck teaches a coating composition comprising 60-90 percent by weight of polyethylene glycol (PEG) with an average molecular weight of 1000-9000, and 10-40 percent by weight of one or more synthetic or natural resins and gums which are miscible in a solution of PEG at temperatures of 45° C.–200° C. The application method described comprises tumbling tablets in a rotating coating pan, preheating and maintaining the tablets at a temperature of 30° C. to 40° C., continuously applying the molten composition at temperatures of 60° C. to 130° C. onto the tablets until the desired coat thickness is obtained, and then tumbling/cooling the tablets to congeal the coating.

A second publication, Tuerck et al, Formula Modifications in a Solvent-Free Tablet Film Coat, *J. Pharm. Sci.*, Vol. 62, 1534–37 (1973), describes the results of a screening study of 17 materials, including stearic acid, used to modify a basic hot-melt composition containing either 10 percent shellac and 90 percent PEG or 20 percent shellac and 80 percent PEG. The materials were added individually to the two basic hot-melt compositions at a level of 10 percent of the total composition. No other levels were evaluated. The modified compositions were then applied to tablets using the equipment and process described in the Tuerck patent. Of the additives evaluated, Tuerck et al found that only castor oil, cocoa butter and isopropyl myristate improved the basic formulations.

Polyethylene glycol has a somewhat unpleasant burning taste. It has also been found, that a high content of polyethylene glycol in tablet coatings result in tablets that are rough looking or bumpy textured. Moreover, increasing the polyethylene glycol content past certain percentages appears to decrease the durability of the coating as evidenced by cracking during handling. In general, PEG is not used in tablet coating at high concentrations because of objectionable taste and odor. Thus, it would be desirable to formulate a solvent-free coating that eliminated the disadvantages resulting from high levels of polyethylene glycol.

Accordingly, it is an object of this invention to provide a process for producing directly compressible cholestyramine tablets.

Another object of this invention is to provide agglomerated cholestyramine particles that can be directly compressed into a tablet having essentially no excipients or additives.

Yet another object of this invention is to provide a smooth, solvent-free coating that contains low amounts of polyethylene glycol and can be used to coat tablets such as cholestyramine.

SUMMARY OF THE INVENTION

Directly compressible cholestyramine agglomerated particles (agglomerates) are provided. The agglomerates are made up of numerous small, irregularly-shaped jagged-edged fragments having relatively few smooth or flat surfaces with a moisture content ranging from about 8 percent to about 14 percent by weight. Pharmaceutical tablets predominantly comprising the above-described cholestyramine agglomerated particles are also provided as well as a process for making the directly compressible cholestyramine agglomerates.

A solvent-free coating is also provided, which coating comprises from about 60 percent to about 95 percent by weight of stearic acid, and from about 5 percent to about 40 percent by weight of polyethylene glycol. The solvent-free coating can be used to coat pharmaceutical tablets, including cholestyramine tablets prepared in accordance with this invention.

DETAILED DESCRIPTION OF THE INVENTION

As discussed above, cholestyramine is extremely hygroscopic, and therefore should be protected from contact with the mucous membrane of the mouth. Accordingly, tablets prepared in accordance with this invention comprise a direct compression cholestyramine "core tablet" encapsulated in a solvent-free coating such as the coating described below.

The cholestyramine tablet inner core comprises directly compressed cholestyramine agglomerates, said agglomerates formed from small irregularly-shaped, jagged-edged particles of cholestyramine with relatively few large smooth or flat surfaces. Preferably, the cholestyramine agglomerates have a moisture content of 8-14%, a tapped bulk density of 0.45 to 0.5 g/ml, and when directly compressed provide an inner core having a hardness of 18-26 SCU.

The solvent-free coating comprised of from about 60 to 90 percent by weight of stearic acid and from about 5 to 40 percent by weight of polyethylene glycol provides an easily swallowable tablet.

I. The Direct Compression Cholestyramine Core Tablet

It has been found that cholestyramine agglomerated particles of a particular shape and water content are directly compressible into pharmaceutical tablets having acceptable hardness values. In particular, it has been found that cholestyramine particles are directly compressible when they consist of agglomerated particles made up of numerous small, irregularly-shaped, jagged-edged fragments having few, if any, smooth or flat surfaces and a moisture content of from about 8-14 percent by weight. The bulk density of the agglomerated particles is from about 0.35-0.37 g/mL when loose, as determined by Sargent-Welch Volumeter apparatus, and from about 0.45-0.5 g/mL when tapped, as determined by a Tap-Pak Volumeter.

Figure 7:
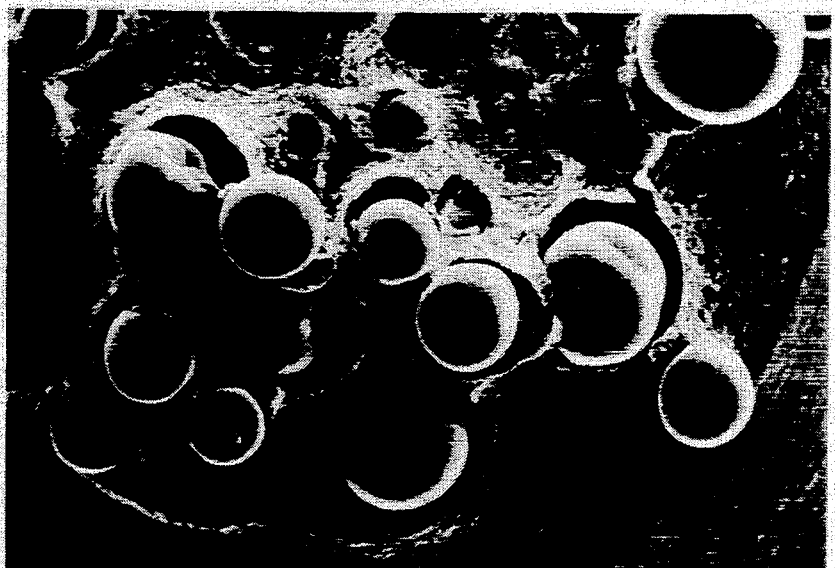
FIG. 7 is a scanning electron photomicrograph of DOWEX 1-X2 cholestyramine beadlets that can be processed according to the instant invention to provide cholestyramine agglomerates (FIG. 9) which can be directly compressed in accordance with this invention.
Figure 8:
FIG. 8 is a scanning electron photomicrograph of AMBERLITE XE-268P cholestyramine beadlets which can be processed according to the instant process of the invention to provide cholestyramine agglomerates (FIG. 10) which can be directly compressed in accordance with this invention.

A process which can be used for producing the above-described cholestyramine particles is as follows. Wet (approximately 70 percent water) cholestyramine beadlets are hammer milled wet as is. Particularly preferred cholestyramine beadlet raw material can be obtained from Dow Chemical Company under the trade name DOWEX 1-X2 Resin (herein DOWEX beadlets). As shown in the FIG. 7 photomicrograph (300x), these beadlets are generally spherical in shape with a few beadlets having a partially collapsed surface. AMBERLITE XE-268P cholestyramine beadlets (herein AMBERLITE beadlets) supplied by Rohm and Haas, Mozzanica, Italy, can be used but cholestyramine particles prepared therefrom according to the instant process require appreciably greater compression forces to provide durable tablets. As shown in the FIG. 8 photomicrograph (300x), AMBERLITE beadlets are also generally spherical in shape but are distinguished from DOWEX beadlets (FIG. 7) in that the AMBERLITE beadlets are fractured resulting in approximate beadlet half-spheres having relatively large, smooth, flat surfaces at the area of the fracture whereas DOWEX beadlets have no visable fractures with a few beadlets having partially collapsed surfaces. The beadlets are passed through a Mikro-Pulverizer either type 2-DH or 1SH from Pulverizing Machinery, Summit N.J. The mill is equipped with ¼" jump gap screen and six inlets open on the grinding chamber. Other types of conventional milling equipment are suitable with proper adjustment.

The hammer milled beadlet material is then dried to the desired moisture content of from about 8 percent to about 14 percent by weight, preferably from about 9 percent to about 13 percent by weight, and most desirably, from about 12–13 percent in a fluidized bed or other drying equipment. When drying the milled material in a fluidized bed such as an Aeromatic or Procedyne Drier the inlet temperature should be preferably set at 48° C. to 58° C. and most preferably at 53° C. However, it is possible to dry at temperatures outside the preferred range. For instance, temperatures in excess of 58° C. can be used at the start of the drying cycle but must be decreased to within the 48° C. to 58° C. range when the moisture content of the material approaches 8–14 percent. Failure to reduce the temperature will result in resin decomposition with trimethylamine formation. Temperatures below 48° C. can be used but will prolong the drying time and accordingly are not economically feasible. During drying, the milled material has a tendency to form clumps and is sized to the desired cholestyramine agglomerated particle size by using a Model D Fitzmill equipped with a #000 plate, impact hammers and set at high speed. Other mills conventionally used for sizing particles can also be employed.

Figure 1:
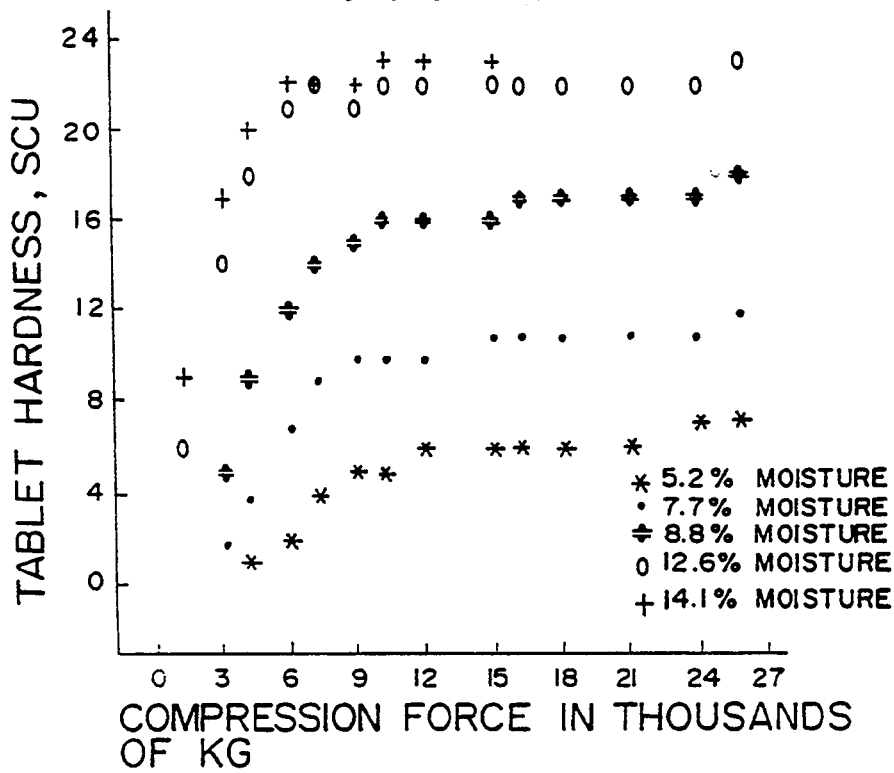
FIGS. 1-4 are graphs showing the relationship between moisture content, compression force and average tablet hardness for cholestyramine tablets prepared in accordance with this invention.

Drying is critical to providing tablets of suitable durability. For example, as shown in FIG. 1, when the above-described milled material has a moisture content of about 9 percent, 3000 Kg of compression results in a tablet having a hardness of about 5 Strong Cobb Units (SCU). If the moisture content is increased to about 12.5 percent, the same compression results in a tablet having a hardness of about 14 SCU. Increasing the pressure to 4000–6000 kg provides tablets having a hardness of about 18–22 SCU which is within the 18–26 SCU range desired for large-scale production. Increasing the moisture content above about 12.5 percent yields little, if any, appreciable difference in hardness at compression forces of 6000 Kg and above. Moisture contents of above about 14 percent may result in lubrication problems during compression.

Figure 2:
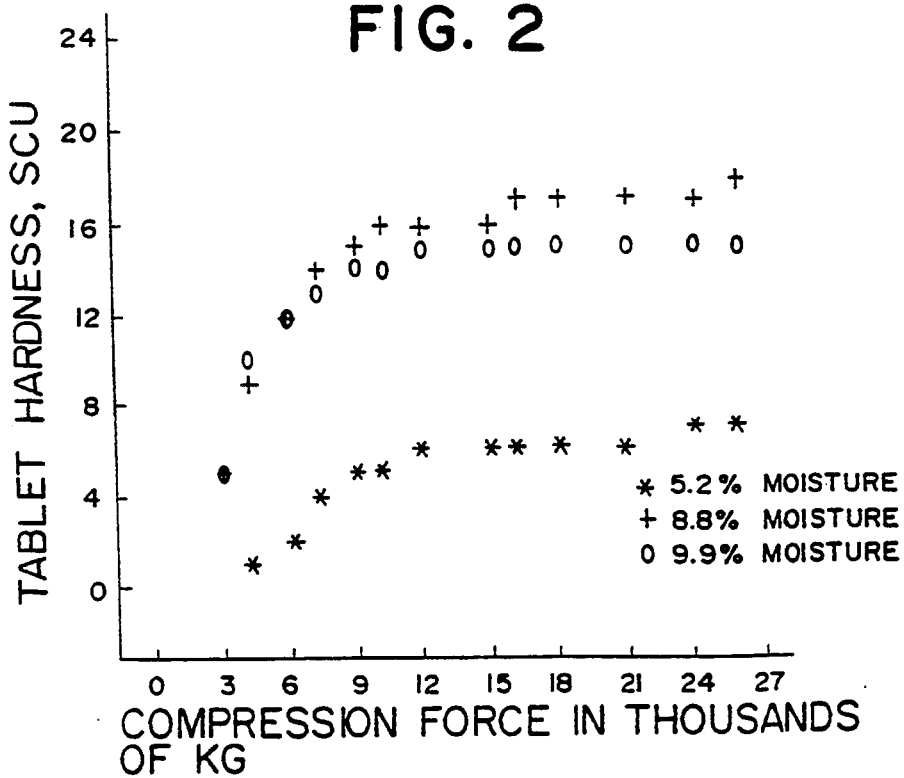
Figure 4:
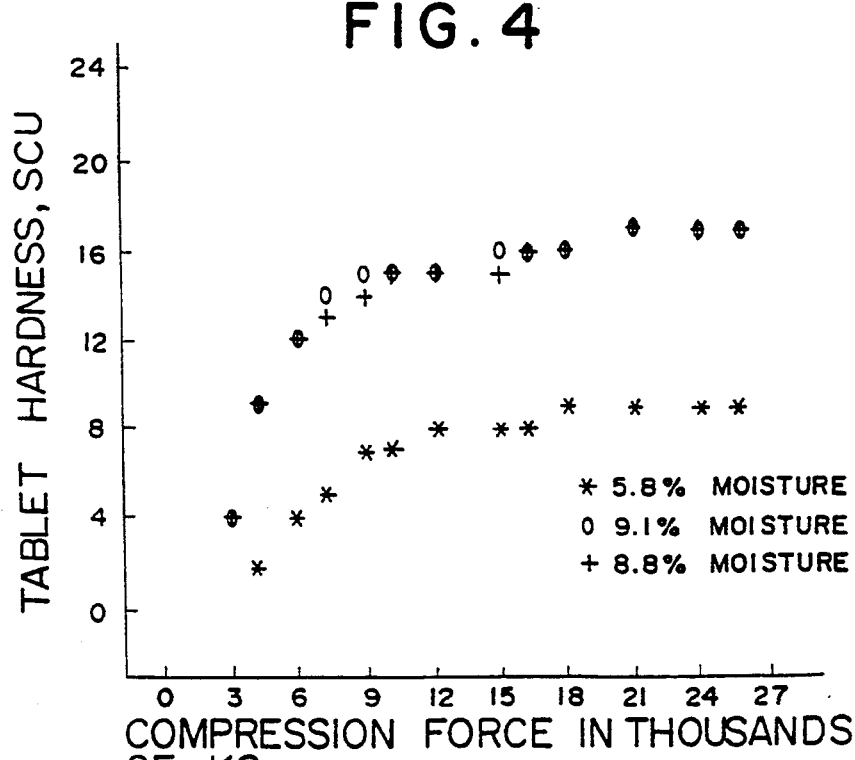

Conveniently, cholestyramine particles that have been dried to moisture contents below the preferred ranges can simply be rewetted to within the preferred ranges to provide compressibility similar to that of particles which have not been overdried as shown in FIGS. 2 and 4.

Adding a lubricant such as magnesium stearate is helpful in facilitating ejection of the tablets from the dies after compression and preventing sticking of the tablets to the punch faces. An amount of about 0.3 percent by weight has provided acceptable results, with higher amounts tending to provide diminished hardness values.

Optionally, other diluents can be added to the direct compressible cholestyramine particles. However, such diluents are not necessary because a core tablet blend of cholestyramine having the above-described moisture contents is sufficiently compressible to provide acceptable core tablets. Moreover, the presence of other diluents might have a detrimental effect on hardness, disintegration and/or stability. Other diluents include pregelatinized corn starch, lactose monohydrate, microcrystalline cellulose, calcium phosphate, ungelatinized corn starch, and dextrose. The core tablet formulation can also contain disintegrants, which are substances that facilitate disintegration of the tablet in the presence of water or biological fluids, and thus hasten the release of the active ingredients. The core tablet blend can also contain glidants, which are compounds used to improve the flow of the core tablet blend and minimize tablet weight variation. Such additional ingredients will be readily apparent to those skilled in the art and determining the optimum levels of such ingredients is well within the ordinary skill of such persons using routine experimentation.

As described above, the process for making cholestyramine agglomerates from cholestyramine beadlets wherein said agglomerates can be directly compressed into tablets comprises (a) passing the wet beadlets through a hammer mill micropulverizer to grind the beads;

(b) drying the ground beads at 48° C. to 58° C. to a moisture level of 8 to 14 percent by weight;

(c) sizing the dried material to provide cholestyramine agglomerates which can be directly compressed into tablets, said agglomerates being irregularly-shaped and jagged-edged with relatively few flat surfaces.

The cholestyramine agglomerates, together with any additional ingredients, are blended and tableted using conventional tableting means which will be readily apparent to those skilled in the art.

II. The Solvent-Free Coating

As mentioned above, cholestyramine is hygroscopic and must therefore be coated to be swallowable. Unfortunately, conventional coating techniques (aqueous and organic solvents) cannot be used to coat cholestyramine because the resin has a high affinity for the solvents. Accordingly, a novel coating has been discovered that can be applied as a hot melt, and when cool, provides a wax-like coating that facilitates swallowing by slightly delaying tablet disintegration. The coating has a melting point of approximately 55° C.–60° C.

The novel coating comprises from about 60–95 percent by weight of stearic acid, and from about 5–40 percent by weight of polyethylene glycol, which provides water miscibility. Preferably, the coating comprises 80–95 percent by weight of stearic acid and from 5–20 percent by weight of polyethylene glycol. Optionally, the coating can also contain from about 10–20 percent by weight of partially hydrogenated vegetable oil such as soybean, cottonseed, etc. The addition of the latter ingredient provides a coated tablet having better defined shape and edges. A suitable partially hydrogenated soybean oil is available from Durkee Foods under the tradename DURKEE 17. A particularly good coating comprises about 80 percent stearic acid, about 15 percent partially hydrogenated soybean oil, and about 5 percent polyethylene glycol.

The coating can, of course, contain other additives such as coloring, flavoring and processing agents. Such additives will be readily apparent to those skilled in the art.

The general process for applying the coating is described in Tuerck, U.S. Pat. 3,383,237, incorporated herein by reference, and consists of melting and mixing the coating ingredients, preheating the tablets, and applying the melted coating using a spray apparatus until sufficient coat is applied to provide the desired tablet disintegration time. Generally a coating of approximately 50–150 mg per gram tablet is satisfactory with an average coat weight of 80–100 mg preferred. The basic equipment for this process comprises a coating pan (preferably baffled) with a source for heated process air, a heated apparatus for melting and pumping/recirculating the coating materials, and a spraying system utilizing heated atomizing air to apply the coating materials.

Examples 1 and 2 illustrate the dramatic effect of moisture content on the compressibility of cholestyramine agglomerates in accordance with this invention.

EXAMPLE 1

Effect of Moisture on Tablets Prepared From Cholestyramine Agglomerates Obtained by Wet Milling DOWEX Beadlets An experiment was conducted to determine the influence of moisture content on the compression characteristics of cholestyramine agglomerates in accordance with this invention. Ground, dried cholestyramine was prepared from DOWEX beadlets as described above. The moisture content was 8.8 percent as determined by loss on drying (16 hours, 70° C., vacuum oven). A portion of the material was held as is. The moisture content of other portions was altered to achieve target moisture contents of about 5.0 percent, 7.5 percent, 12.0 percent, or 15.0 percent. This was accomplished by drying the material in a forced air oven (22 hours at 53° C. then 8 hours at 65° C.) or by drying in a vacuum oven at 70° C. for 5.5 hours or by adding calculated amounts of water. When water was added, the material was blended for 5 minutes in a 0.67 cubic foot Lodige mixer at 210 rpm with the chopper off. The wetted material was then hand screened through a 30 mesh screen and blended for an additional 5 minutes. In addition, the moisture content of the vacuum dried material was brought back to the original moisture content by adding a calculated amount of water and blending as previously described. All samples were held in a closed glass container for at least 24 hours prior to use.

Tablet blends were prepared by mixing a common blend of inactive excipients with each portion of cholestyramine in the Lodige mixer for 5 minutes at 210 rpm with the choppers off. The blends were compressed on an instrumented Manestry D3B tablet press at different compression forces using 0.835" x 0.360" capsule shaped tooling. The compression forces used to make tablets were recorded. The hardness of resulting tablets were measured with a Pharmatest Hardness Tester (Model HT-300).

Results and Discussion

Compression profiles comparing compression force and resulting tablet hardness for each tablet blend are illustrated in FIG. 1. These results clearly demonstrate that cholestyramine moisture content affects the compressibility of the tablet blend, i.e., as the moisture content increased, harder tablets could be produced and less compression force was required to achieve comparable tablet hardnesses. This effect diminished, however, when the moisture content exceeded 12.6 percent and no remarkable difference was obvious between blends containing cholestyramine 12.6 percent or 14.1 percent moisture contents.

The only tableting problem occurred when compressing the blend containing cholestyramine with the highest moisture content (14.1 percent). This blend caused the tablet tooling to bind in the dies. The magnesium stearate concentration was increased to 7 mg per tablet, which eliminated munch binding but adversely affected compression. The highest hardness attainable was 10.5 SCU.

When the moisture content of the driest cholestyramine portion (5.2 percent) was restored to near its original moisture content (9.9 percent), the resulting blend had a compression profile nearly the same as the blend made with the original cholestyramine. This phenomenon is illustrated in FIG. 2 and indicates that overdried batches of cholestyramine can be rendered compressible by adding appropriate amounts of water. Trimethylamine (TMA) odor was detected from the overdried cholestyramine (5.2 percent). The TMA content for the 5.2 percent material was 41 ppm and 17 ppm for the original material. Thus, overdrying of cholestyramine will result in higher TMA concentrations.

In conclusion, this example illustrates how the moisture content of cholestyramine agglomerates in accordance with this invention influences the compression characteristics of tablets made therefrom. The compression characteristics of tablet blends will improve as the moisture content is increased up to approximately 12.6 percent. Overly dried batches of cholestyramine can be salvaged, in terms of compressibility, by adding appropriate amounts of water.

EXAMPLE 2

Effect on Tablet Hardness of Adding Moisture To Overly Dried Cholestyramine Agglomerates Obtained by Wet Milling DOWEX Beadlets Example 1 was repeated using a different batch of DOWEX beadlets to determine reproducibility of the results. The moisture content was 9.1 percent as determined by loss on drying (16 hours, 70° C., vacuum oven). A portion of the material was held as is. The moisture content of other portions was altered to achieve target moisture contents of about 5.0 percent, 7.5 percent, 12.0 percent, or 15.0 percent. This was accomplished by drying the material in a vacuum oven at 70° C. for either 2.5 hours or 5.5 hours or by adding calculated amounts of water. When water was added, the material was blended for 5 minutes in a 0.67 cubic foot Lodige mixer at 210 rpm with the chopper off. The wetted material was then hand screened through a 30 mesh screen and blended for an additional 5 minutes. In addition, the moisture content of the vacuum dried material was brought back to near its original moisture content by adding a calculated amount of water and blending as previously described. All samples were held in a closed glass container for at least 24 hours prior to use.

Tablet blends were prepared by mixing a common blend of inactive excipients with each portion of cholestyramine in the Lodige mixer for 5 minutes at 210 rpm with the choppers off. The blends were compressed on an instrumented Manesty D3B tablet Dress at different compression forces using 0.835 inch x 0.360 inch capsule shaped tooling. The compression forces used to make tablets were recorded. The hardness of resulting tablets was measured with a Pharmatest Hardness Tester (Model HT-300).

Results and Discussion

Figure 3:
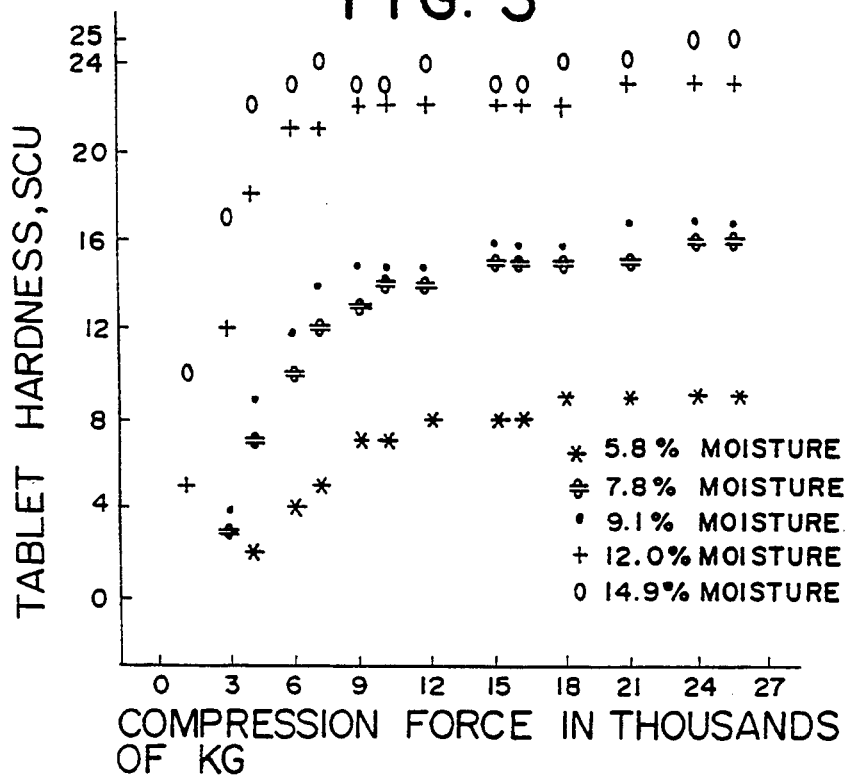

Compression profiles comparing compression force and resulting tablet hardness for each tablet blend are illustrated in FIG. 3. The profiles were similar to those from Example 1 (FIG. 1) and clearly demonstrate that cholestyramine moisture content affects the compressibility of cholestyramine agglomerates in accordance with this invention, i.e., as the moisture content increased, harder tablets could be produced and less compression force was required to achieve comparable tablet hardnesses. This effect diminished, however, when the moisture content exceeded 12.0 percent and no remarkable difference was obvious between the blends containing cholestyramine with 12.0 percent or 14.9 percent moisture contents.

The only tableting problem occurred when compressing the blend containing cholestyramine with the highest moisture content (14.9 percent). This blend caused the tablet tooling to bind in the dies. The magnesium stearate content was increased up to 6 mg per tablet, but did not eliminate punch binding. Moreover, compression was adversely affected by increasing the magnesium stearate, i.e., the highest hardness attainable was 12.5 SCU. Results from Example 1 indicated that 7 rag per tablet eliminated punch binding but compression was affected to a greater degree. That is, only a hardness of 10.5 SCU was attainable.

When the moisture content of the driest cholestyramine portion (5.8 percent) was restored to near its original moisture content (8.8 percent), the resulting blend has a compression profile nearly the same as the blend made with the original cholestyramine. The profiles are illustrated in FIG. 4 and are in agreement with Example 1 (FIG. 2) which indicates that overdried batches of cholestyramine can be rendered compressible by adding appropriate amounts of water. TMA odor was again detected from the overdried cholestyramine (5.8 percent). The TMA content for the 5.8 percent material was 48 ppm and 10 ppm for the original material. Thus, as observed in Example 1, over-drying of cholestyramine will result in higher TMA concentrations.

In conclusion Example 2 illustrates that the moisture content of the ground, dried cholestyramine particles in accordance with this invention influences the compression characteristics of tablets made therefrom. The compression characteristics of tablet blends will improve as the moisture content is increased up to approximately 12.0 percent. Overly dried batches of cholestyramine can be salvaged, in terms of compressibility, by adding appropriate amounts of water. The results of this study are comparable to the results from Example 1.

Examples 3, 4, and 5 illustrate that cholestyramine agglomerates in accordance with this invention are directly compressible, and that cholestyramine particles that are not in accordance with the invention do not have similar properties.

In these examples, AMBERLITE powdered resin was compared with cholestyramine agglomerates obtained according to the instant process. As shown in TABLE I below, the particle size of the of the DOWEX agglomerates (Z0620), AMBERLITE agglomerates and AMBERLITE powdered resin (R1734) are approximately the same.

TABLE I

PARTICLE SIZE DISTRIBUTION
(Alpine Sieve Apparatus)

| | Percent Retained | | |
|---|---|---|---|
| Mesh Size | Z0620 | AMBERLITE Agglomerates | R1734 |
| 60 | 5 | 0 | 0 |
| 80 | 2 | 6 | 0 |
| 100 | 6 | 2 | 3 |
| 200 | 37 | 36 | 30 |
| 325 | 33 | 46 | 34 |
| Thru 325 | 17 | 10 | 33 |

Figure 9:
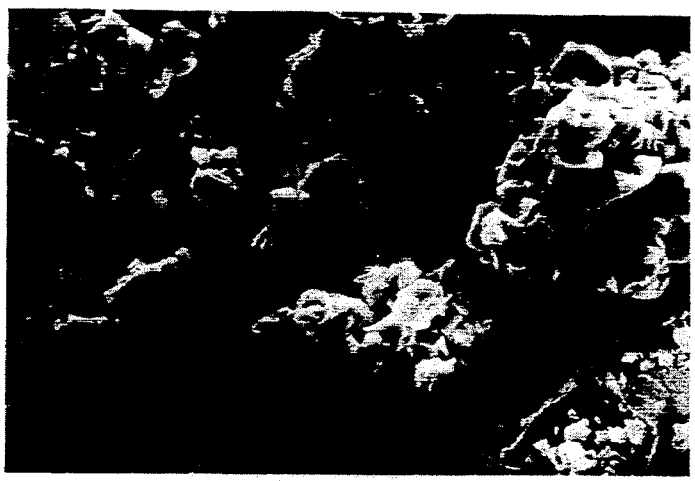
FIG. 9 is a scanning electron photomicrograph of cholestyramine agglomerates prepared from DOWEX 1-X2 cholestyramine resin beadlets that can be directly compressed into a tablet in accordance with this invention.
Figure 10:
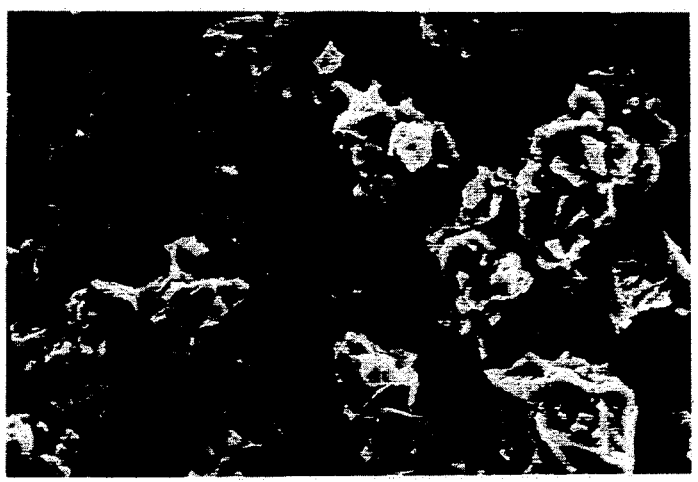
FIG. 10 is a scanning electron photomicrograph of cholestyramine agglomerates prepared from AMBERLITE XE-268P resin beadlets that can be directly compressed into a tablet in accordance with this invention.
Figure 11:
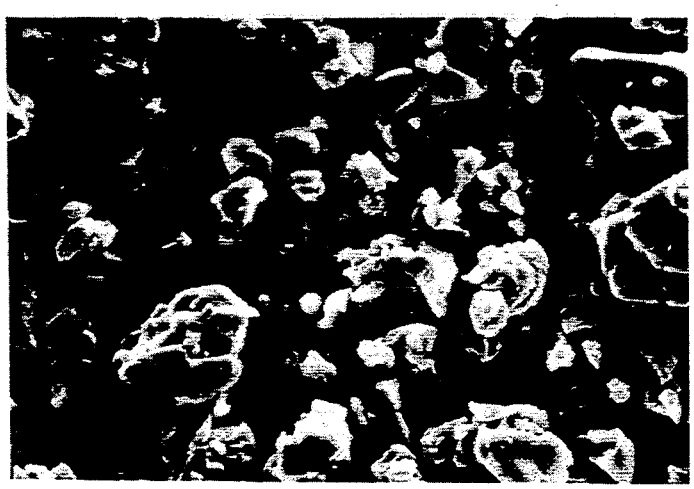
FIG. 11 is a scanning electron photomicrograph of cholestyramine AMBERLITE XE-268P powdered resin particles, herein R1734, which cannot be directly compressed.

However, scanning electron photomicrographs (250x) (FIGS. 9, 10, and 11) of the agglomerates and R1734 powdered resin taken at a magnification of 250X indicate significant differences in appearance of the particles. As illustrated by FIG. 9, the overall size of the Z0620 particles is similar to or slightly larger than the AMBERLITE agglomerates or R1734 powdered resin. FIG. 10 illustrates that AMBERLITE agglomerates consist of small particles attached to a larger core particle. As seen in FIG. 11, the R1734 powder has a predominance of large single particles with very little agglomerated material. Differences in shape are also shown in the photomicrographs. The Z0620 particles (FIG. 9) are irregular in shape, as are particles from the other two powders. However, the Z0620 particles have jagged edges and relatively few large smooth/flat surfaces. The AMBERLITE particles (FIG. 10) are more like the Z0620 agglomerates than the R1734 powdered resin but show evidence of some particles having smooth/flat surfaces. The R1734 powder (FIG. 11) predominantly consists of particles having relatively large, smooth/flat surfaces. It is evident, therefore, that particles suitable for direct compression should consist of agglomerates formed from many small, irregularly-shaped, jagged-edged particles. These particles are more cohesive and thus have the propensity to agglomerate and easily bond during compression, to produce durable tablets at low compression forces.

The bulk density of the DOWEX and AMBERLITE agglomerates and AMBERLITE powdered resin was determined for comparison purposes. Typical results in TABLE II below show that the Z0620 is the least dense, followed by the AMBERLITE agglomerates and finally the R1734 powder which has the highest (tapped) density.

TABLE II

BULK DENSITY

| | Density (g/mL) | |
|---|---|---|
| Powder | Loose* | Tapped** |
| Z0620 | 0.363 | 0.478 |
| AMBERLITE agglomerates | 0.370 | 0.485 |
| R1734 | 0.382 | 0.525 |

*Sargent Welch Volumeter
**Tap-Pak Volumeter

Thus, the cholestyramine agglomerates suitable for direct compression have a loose bulk density of 0.35 to 0.37 g/mL and a tapped bulk density of 0.45 to 0.5 g/mL with a preferred tapped bulk density of 0.47 to 0.49 g/mL.

EXAMPLE 3

Compressibility Comparison of AMBERLITE R1734 Powdered Resin and Cholestyramine Agglomerates of this Invention Two different lots of AMBERLITE R1734 powdered resin were used to prepare two batches of 1 g cholestyramine tablets. The first lot contained about 9.2 percent by weight moisture and the second lot contained about 8.4 percent by weight moisture. The highest attainable hardness for the tablet batches were 7.0 SCU and 7.5 SCU, and the tablets produced were not durable because they failed a friability test of 100 drops. In contrast, when particles in accordance with this invention were used in nearly identical compositions, a tablet hardness of 21 SCU could be achieved. Tablets compressed within the in-process range of 18 SCU to 26 SCU passed the friability test.

Another lot of AMBERLITE R1734 powdered resin having an average moisture content of 9.0 percent by weight water was used in an unsuccessful attempt to manufacture 1 g cholestyramine core tablets. The highest attainable tablet hardness at compression force of about 7 to 9 kilograms was only 10 SCU and the tablets were not durable. In contrast, several batches of core tablets were successfully produced with cholestyramine agglomerates according to this invention having moisture contents ranging from 7.6 percent to 10.5 percent by weight. The tablets were compressed to 22 SCU (considered optimum hardness) and were sufficiently durable to pass the friability test and withstand a coating process.

This study demonstrates that selection of cholestyramine agglomerates according to the instant invention is critical to providing directly compressed tablets of suitable hardness.

EXAMPLE 4

Figure 5:
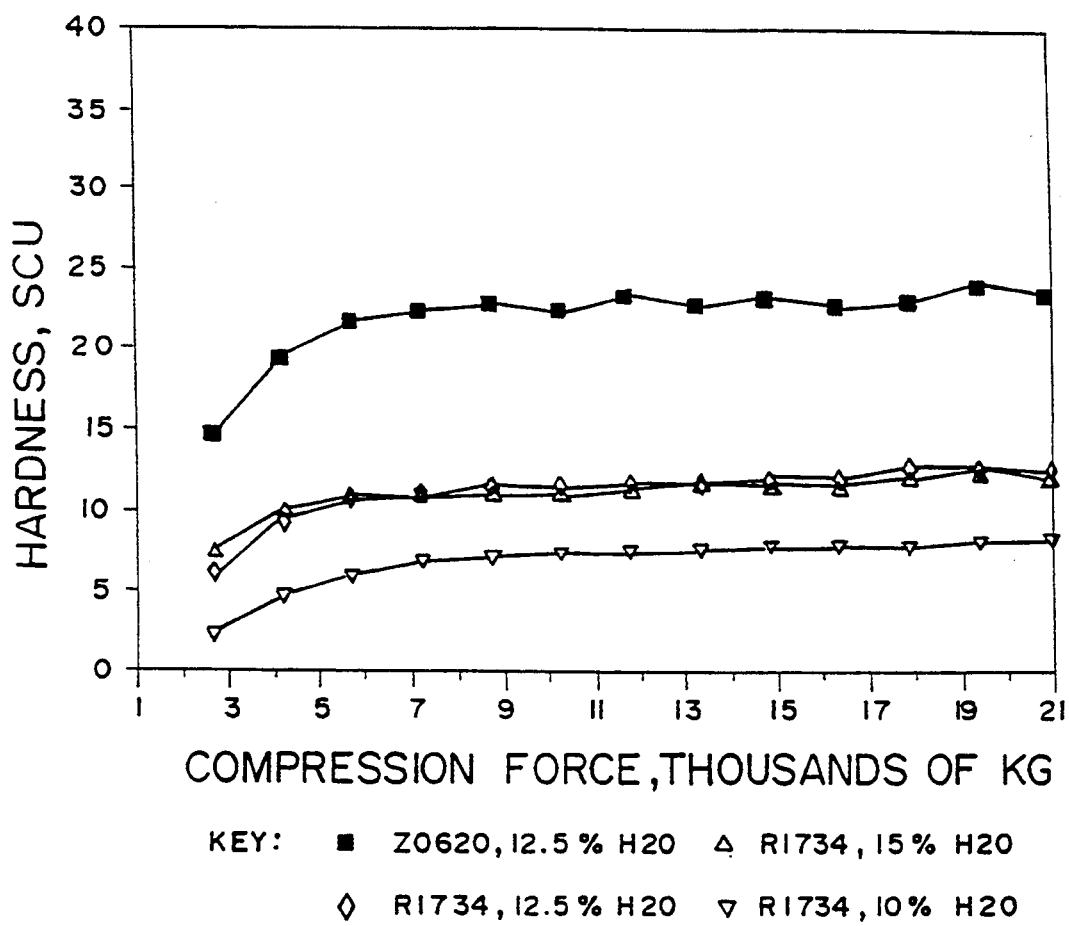
FIG. 5 is a graph showing the relationship between compression force and average tablet hardness for cholestyramine tablets prepared from cholestyramine agglomerates (Z0620) in accordance with this invention versus cholestyramine tablets prepared from cholestyramine powdered particles (R1734) not in accordance with this invention.

Compressibility Comparison of the Effect of Moisture on Tablets Prepared From AMBERLITE R1734 Powdered Resin and Cholestyramine Particles of this Invention An experiment was performed to compare the compression properties of tablets prepared from cholestyramine agglomerates of this invention having 12.5 percent by weight moisture with 3 lots of the AMBERLITE R1734 powdered resin having 10 percent, 12.5 percent and 15 percent by weight moisture. Results are shown in FIG. 5.

This study demonstrates that compression characteristics of the AMBERLITE R1734 powdered resin are unacceptable regardless of moisture content. The highest attainable tablet hardness of 12-13 SCU was achieved only by using excessive compression force. In contrast, directly compressed tablets manufactured with cholestyramine agglomerates (herein designated DOWEX Z0620) obtained from DOWEX beadlets according to this invention easily met the compression criteria of 18 to 26 SCU, and in fact could be compressed to hardness values exceeding 18 SCU without excessive compression force.

EXAMPLE 5

Compressibility Comparison of Cholestyramine Agglomerates Obtained From DOWEX and AMBERLITE Beadlets According to this Invention and AMBERLITE R1734 Powdered Resin An experiment was performed to compare compression properties of cholestyramine agglomerates of this invention with AMBERLITE powdered resin (R1734). The cholestyramine agglomerates and AMBERLITE R1734 powdered resin had a moisture content of 9–10 percent.

For purposes of large-scale manufacturing, tablets must have SCU average hardness values of 18 to 26, preferably 20 to 24 and most preferably 22 to 23 to withstand handling during coating and packing.

Figure 6:
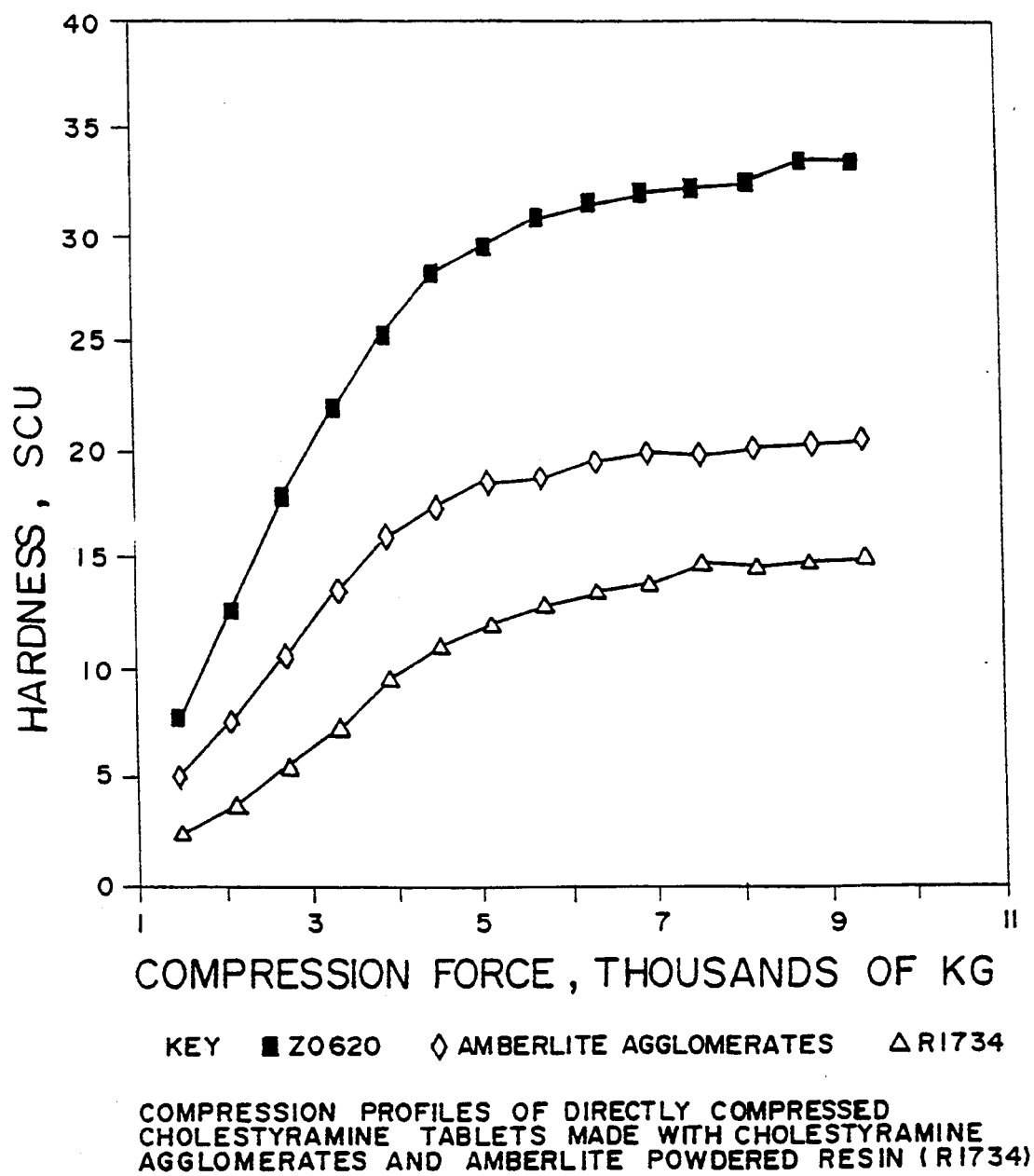
FIG. 6 is a graph showing the relationship between compression force and average tablet hardness for directly compressed cholestyramine tablets prepared from cholestyramine agglomerates Z0620 and AMBERLITE agglomerates obtained from DOWEX 1-X2 and AMBERLITE XE-268P beadlets, respectively, in accordance with this invention and AMBERLITE XE-268P powdered resin particles (R1734).

FIG. 6 sets out the results of the study, and it is evident that in the acceptable hardness range, only the DOWEX agglomerates (Z0620) and AMBERLITE agglomerates obtained according to the instant process can be directly compressed to provide tablets having the desired hardness. FIG. 6 also illustrates that DOWEX beadlets are preferred over AMBERLITE beadlets as raw material in that relatively harder tablets are obtained with DOWEX particles.

This comparative study clearly demonstrates that direct compressed tablets made with AMBERLITE R1734 powdered resin are distinctive inferior with respect to tablet hardness and durability compared to tablets made from cholestyramine agglomerates of the instant invention.

EXAMPLE 6

Preparation of Directly Compressed, Coated Cholestyramine 1.0 gram Tablets

Tablets were prepared by compressing a mixture of cholestyramine (99.7%) and magnesium stearate (0.3%) into 0.360 inch x 0.835 inch capsule-shaped tablets, weighing approximately 1120 mg each.

The molten coating composition, consisting of stearic acid (80%), partially hydrogenated soybean oil (15%), and 5% polyethylene glycol 3350 (molecular weight range 3015–3685), was prepared by combining the components in a container and heating them to a temperature of 90° –100° C., while stirring, to form a uniform molten mixture.

Approximately 6000 tablets (6.7 kg) were placed in a 24-inch Accela-Cota pan and warmed to a temperature of 40° –45° C. by introducing heated air into the pan. The heated tablets were then tumbled in the pan (rotating at 10 rpm), and with the heated air to the pan continuing, were coated with the molten coating material. The apparatus used to apply the coat to the tablets consisted of a heated pump/transfer line system connected to a 4-nozzle pneumatic spray system. Heated air at 110° –120° C. was supplied to the spray system to heat the nozzles and atomize the molten coating material. The coat application continued until a coat weighing approximately 130 mg/tablet was coated. This application required 40–45 minutes to complete. The coated tablets were then allowed to tumble and cool for about 10 minutes.

What is claimed is:

1. A cholestyramine tablet inner core consisting of directly compressed cholestyramine agglomerates and about 0.3 percent by weight of a lubricant, said agglomerates having a moisture content of 8 to 14 percent and formed from many small irregularly-shaped, jagged-edge particles with relatively few large smooth or flat surfaces wherein said agglomerates, when directly compressed, provide an inner core having a hardness of at least 18 SCU.

2. A cholestyramine tablet inner core of claim 1 wherein said agglomerates have a tapped bulk density of 0.45 to 0.5 g/ml.

3. A cholestyramine tablet inner core of claim 1 wherein said agglomerates, when directly compressed, provide an inner core having a hardness of 18 to 26 SCU.

4. A cholestyramine tablet inner core of claim 1 wherein said lubricant is magnesium stearate.

5. A cholestyramine tablet inner core consisting of directly compressed cholestyramine agglomerates and about 0.3 percent by weight of magnesium stearate, said agglomerates having a tapped bulk density of 0.45 to 0.5 g/ml and a moisture content of 8 to 14 percent and formed from many small irregularly-shaped, jagged-edge particles with relatively few large smooth or flat surfaces wherein said agglomerates, when directly compressed, provide an inner core having a hardness of 18 to 26 SCU.

* * * * *